United States Patent [19]
Balkus, Jr. et al.

[11] Patent Number: 5,830,429
[45] Date of Patent: Nov. 3, 1998

[54] METAL SILICATE COMPOSITIONS AND CATALYSTS

[75] Inventors: Kenneth J. Balkus, Jr., The Colony; Alexei G. Gabrielov, Houston, both of Tex.

[73] Assignee: Board of Regents, The University of Texas System, Austin, Tex.

[21] Appl. No.: 599,536

[22] Filed: Feb. 6, 1996

[51] Int. Cl.⁶ .............................. C01B 39/04; B01J 29/06
[52] U.S. Cl. ........................ 423/702; 423/703; 423/713; 423/718; 502/62; 502/63; 502/64; 502/202
[58] Field of Search .................................... 423/702, 703, 423/718, DIG. 30, 713; 502/62, 63, 64, 214, 202

[56] References Cited

U.S. PATENT DOCUMENTS

| | | | |
|---|---|---|---|
| 4,440,871 | 4/1984 | Lok et al. | 502/214 |
| 4,556,549 | 12/1985 | ValyocsIk | 423/702 |
| 4,568,654 | 2/1986 | Valyocsik | 502/62 |
| 4,744,970 | 5/1988 | Lok et al. | 423/702 |
| 5,106,801 | 4/1992 | Zones et al. | 502/64 |
| 5,156,829 | 10/1992 | McCullen et al. | 423/718 |
| 5,167,942 | 12/1992 | Balkus et al. | 423/705 |
| 5,316,753 | 5/1994 | Nakagawa | 423/706 |
| 5,334,367 | 8/1994 | Rosinski et al. | 423/704 |
| 5,489,424 | 2/1996 | Balkus, Jr. et al. | 423/702 |

OTHER PUBLICATIONS

Balkus and Gabrielov, "The Synthesis and Characterization of UTD–1. A Novel Molecular Sieve Containing Bis(Pentamethylcyclopentadienyl) Cobalt (III) Ion," ACS Symposium, Anaheim, CA, USA, Apr. 1995.

International Search Report dated Jun. 24, 1997 (UTTF:069P).

Balkus, Jr. et al., "The Synthesis and Characterization of the Molecular Sieve SAPO–16 as well as Other SAPO and CoAPO Phases Using bis(cyclopentadienyl) cobalt(III) Hydroxide as a Structure Directing Agent", *J. of Porous Materials*, 1:199–206, 1995, no month.

Balkus, Jr., Kenneth J. and Nowinska, Krystyna, "Intrazeolite organometallics Pentamethylcyclopentadienyl rhodium complexes", *Microporous Materials*, 3:665–686, 1995, Mar.

Balkus, Jr., Kenneth J., et al., "Molecular Sieve Synthesis Using Metallocenes as Structure Directing Agents", *Mat. Res. Soc. Symp. Proc.*, 368:369–375, 1995, no month.

Balkus, Jr., K. J., et al., "Synthesis and Characterization of UTD–1: A Novel Zeolite Molecular Sieve", *Petrol Preprints*, 40:296–297, 1995, Apr.

Balkus, Jr., K. J., et al., "The synthesis of UTD–1 and Ti–UTD–8 using Cp*₂CoOH as a structure directing agent", *Stud. Surf. Sci. Catal.*, 97:519–525, 1995, no month.

Balkus, Jr., K. J. and Shepelev, S., "Synthesis of nonasil molecular sieves in the presence of cobalticinium hydroxide", *Microporous Materials*, 1:383–391, 1993, no month.

Haggin, Joseph, "Novel Epoxidation Catalyst–Titanium complex anchored inside zeolite", *C&EN*, p. 6, 1995 Nov.

Maschmeyer, Thomas, et al., "Heterogeneous catalyst obtained by grafting metallocene complexes onto mesoporous silica", *Nature*, 378:159–162, 1995. Nov.

Schuchardt, Ulf, et al., "Cyclohexane oxidation with hydrogen peroxide catalyzed by titanium silicalite (TS–1)", *Stud. Surf. Sci. and Catal.*, 84:1877–1883, 1994, no month.

(List continued on next page.)

*Primary Examiner*—Mark L. Bell
*Assistant Examiner*—Louis M. Troilo
*Attorney, Agent, or Firm*—Arnold, White & Durkee

[57] ABSTRACT

A high silica zeolite (UTD-1) using bis(pentamethylcyclopentadienyl)cobalt(III) hydroxide, Cp*₂CoOH is disclosed. UTD-1 is a large pore molecular sieve having one dimensional channels running in parallel. The synthesis and characterization of silicates incorporating titanium, vanadium, aluminum or boron in the silicate framework is described. Calcined Ti-UTD-1 containing cobalt oxide and the cobalt free molecular sieves are shown to be effective oxidation catalysts. Oxidation of alkanes with hydrogen peroxide and t-butylhydroperoxide (t-BHP) and the room temperature oxidation of cyclohexane to adipic acid are demonstrated.

28 Claims, 8 Drawing Sheets

OTHER PUBLICATIONS

Tatsumi, Takashi, et al., "Factors determining substrate specificity in titanium silicalite catalyzed oxidations", *Stud. Surf. Sci. and Catal.*, 84:1861–1869, 1994, no month.

van de Goor, Gianpietro, et al., "The Cobalticinium Cation $[Co^{III}(\eta^5-C_5H_5)_2]^+$: A Metal–organic Complex as a Novel Template for the Synthesis of Clathrasils", *Z. anorg. allg. Chem.*, 621:311–322, 1995, no month.

Yuen, Lun–Teh, et al., "Product selectivity in methanol to hydrocarbon conversion for isostructural compositions of AFI and CHA molecular sieves", *Microporous Materials*, 2:105–117, 1994, no month.

:
METAL SILICATE COMPOSITIONS AND CATALYSTS

The United States Government owns rights in the present invention pursuant to Grant CHE-9157014 from the National Science Foundation.

BACKGROUND OF THE INVENTION

1. Field of the Invention

The invention relates to novel high silica zeolite compositions and to catalysts prepared from these compounds. The zeolite compositions are prepared using the structure directing metal complex, bis(pentamethylcyclopentadienyl)cobalt (III) hydroxide, $Cp^*_2CoOH$. Catalytic activity is found when various metals are included as part of the zeolite compositions.

2. Description of Related Art

Molecular sieve compounds have been prepared from metallocene templates such as cobalticinium ion, $Cp_2Co^+$ (Balkus et al, 1995; Balkus and Gabrielov, 1995; Balkus et al, 1995; Valyocsik, 1985; Balkus and Shepelev, 1993; van de Goor et al, 1995). The compounds prepared with this structure directing agent are known to crystallize in at least five different topologies. There is compositional variance among these structures, including silicate, aluminum phosphate ($AlPO_4$), silicoaluminum phosphate (SAPO), and metalloaluminum phosphate (MeAPO) phases. Generally, the molecular sieves obtained using the $Cp_2Co^+$ template are small pore, clathrate type materials.

Zeolite based catalysts are a type of molcular sieve that have found use in numerous types of conversions, including recent applications of metal-containing zeolites. For example, titanium incorporated into silicalite 1, silicalite 2 (TS1 and TS2), AlPO-5, AlPO-11 and SAPO-5 in particular have shown promise as oxidation catalysts. However, a disadvantage of these catalysts is the inaccessibility of larger molecules to the interior framework where the metal is located, thereby precluding oxidation of relatively bulky molecules such as fused alicyclic and aromatic compounds.

Mesoporous silicates appear to offer some improvements due to larger pore diameters; however, Maschemeyer et al (1995) report that Ti-MCM-41 has a lower turnover rate for small molecule oxidation conversions compared to a Ti-modified small pore zeolite. Thus the mesoporous silicates do not fulfil the need for efficient oxidation catalysts applicable to both small and larger size molecules.

Mesoporous zeolite-like catalysts that incorporate titanium in the form of titanocene within a pore, but which apparently are not part of the framework, have been reported (Maschemeyer et al, 1995). The titanium atom is sandwiched between two cyclopentadienyl rings and the anion then substituted by alkoxide/siloxide ligands. Applications are reported to include catalytic epoxidation of cyclohexene and pinene (Chemical and Engineering News, 13 November 1995). A turnover frequency of 3 mmole cyclohexene per g catalyst per minute incorporated with a 50% conversion in one hour for epoxidation of the cyclohexene with tertbutyl-hydroperoxide has been reported using these catalysts (Maschemeyer et al. 1995). Although reported to be regenerable, the catalyst was essentially deactivated after about 1.5 hr.

Large pore molecular sieves have been prepared. Bis(pentamethylcyclopentadienyl)cobalt(III)ion, $Cp^*_2Co^+$, used as a template produces several new phases which appear to be large pore materials. For example, the high silica zeolite, UTD-1,is a large pore molecular sieve with channels running in parallel. This particular compound has been prepared using $Cp^*_2Co^+$ as template (Balkus et al, 1995A; Balkus et al, 1995B; Balkus et al 1995C). UTD-1 metal silicates with titanium, vanadium, aluminum or boron incorporated into the framework have also been reported by the same authors. Properties of the titanosilicate, Ti-UTD-1 have been studied in some detail by the Balkus group (Balkus et al, 1995).

Despite the development of molecular sieves as catalysts, there remains a need for new compositions that are not unduly limited by the size of the molecules and particularly that are useful for hydrocarbon conversions. Several types of conversions such as oxidations and acid catalyzed reactions of organic and inorganic compounds would benefit from the development of efficient and relatively inexpensive molecular sieve catalysts.

SUMMARY OF THE INVENTION

The present invention addresses problems inherent in the art by providing novel molecular sieve compounds and particularly novel metal silicates that have use as catalysts for various conversions such as oxidations and acid catalyzed reactions. The new compounds have basic zeolite structures with relatively large pore sizes that are larger than those usually found in zeolites. The compounds may be synthesized using $Cp^*_2CoOH$ as a template.

In certain aspects, the invention relates to modifications of UTD-1. UTD-1 has been previously described in U.S. Pat. No. 5,489,424. The $CP^*_2CoOH$ template can be incorporated with the other components required for UTD-1 synthesis to provide novel catalysts. Added metals, for example, modify the gel chemistry so that the metal is incorporated into the structure. Properties of the metal, such as redox activity, can be taken advantage of in tailoring catalysts for targeted reactions.

One aspect of the present invention is a large pore zeolite similar in some respects to UTD-1, but having distinctly different physical characteristics. This compound has been designated UTD-8. UTD-8 is a microcrystalline high silica molecular sieve that has a nominal pore diameter greater than about 7.2 A. Like UTD-1, it may be prepared using $Cp^*_2CoOH$ as a template, but has an X-ray diffraction pattern distinct from UTD-1. Metals such as titanium may be incorporated into the zeolite framework in relatively large percentages, up to over 9%. It is contemplated that other metals will readily incorporate into the framework; for example, vanadium or boron in a manner similar to incorportion into UTD-1. Additionally, it is expected that other metals such as chromium, manganese, iron, copper, aluminum, cobalt, zinc and gallium that are known to incorporate into the framework of molecular sieves can be used to prepare analogous M-UTD-8 compositions where M represents the metal.

The addition of elements such as boron and aluminum generate anionic charges on the framework which may be balanced by protons. Such silanols possess Bronsted acidity which can be exploited in the catalytic conversion of hydrocarbons. Reactions include cracking, isomerizations, dehydration, etc. In particular, Al-UTD-1 has been shown to be an effective catalyst for the conversion of MEOH to gasoline range hydrocarbons.

The invention also includes catalysts that incorporate elements such as titanium and vanadium in the zeolite structure. These catalysts are typically prepared from UTD-1 that is formed from a bis (pentamethylcyclopentadienyl)cobalt(III)ion template. UTD-1 oxidation catalysts may be prepared from Cp*$_2$CoOH template, sodium hydroxide, and fumed silica to which the appropriate amounts of titanium methoxide or other metal source is added. These catalysts act as oxidation catalysts with Ti-UTD-1 being particularly preferred for this purpose.

The invention also includes catalysts prepared from UTD-8. UTD-8 may be prepared by mixing a CP*$_2$CoOH template and sodium hydroxide, silica and an appropriate amount of metal alkoxide. Exemplary useful elements include vanadium, boron, iron, and the like, as well as titanium which is particularly preferred. Preferred metal sources include metal methoxides; however, metal oxides such as ethoxides or propoxides may also be employed. As discussed, certain of the UTD-8 catalysts, e.g., Ti-UTD-8, function efficiently as oxidation catalysts.

Metals may be incorporated into the disclosed high silica zeolite molecular sieves up to several percent by weight. Typical preparations contain one, two, three or higher percent metals by weight in UTD-1 types of molecular sieves. Higher percentages may be obtained with UTD-8. Titanium, for example, may be incorporated up to at least 9.3% titanium. Boron has been incorporated into the UTD-1 framework up to about 0.5%. The inventors have shown that activity of the catalysts increases with increased amounts of metal in the framework. Thus it is expected that activity of the catalysts can be modified by adjusting the amount of metal incorporated into the molecular framework.

The invention also relates to metal silicate oxidation catalysts. This class of catalysts is prepared by incorporating the appropriate redox metal into the framework of UTD-1 and UTD-8 type molecular sieves. Illustrative examples include metals such as vanadium and titanium as well as boron and aluminum which have been incorporated into these structures. Of course other metals may be incorporated into the structure, including d-transition series metals as well as Group Ib, IIb, III–V metals of the periodic table. In particular, certain redox active methods have been shown to be oxidation catalyst when incorporated in molecular sieves. Examples include iron, cobalt, chromium, manganese, vanadium, etc.

The disclosed high silica, metal molecule sieve compositions are particularly useful as oxidation catalysts for relatively bulky substrates. Exemplary substrates, for example, include cyclohexane, which is efficiently oxidized by tertiary butylhydroperoxide or hydrogen peroxide in the presence of Ti-UTD-1 or Ti-UTD-8 as catalyst. Analagous catalytic reactions are expected for V-UTD-1 and V-UTD-8 and for oxidation catalysts prepared from other approriate metals incorporated into UTD-1 or UTD-8 for oxidizible substrates, such as those oxidized by peroxides or dioxygen.

An advantage of certain of the new catalysts is the surprisingly efficient oxidation of hydrocarbons such as cyclohexane. Thus, Ti-UTD-1 at room temperature efficiently converts cyclohexane to cyclohexanone as the major product with adipic acid and cyclohexanol as minor products. Suprisingly, longer reaction periods for oxidation of cyclohexane using Ti-UTD-1 catalyst in the presence of t-butylhydroperoxide resulted in a 12% conversion to adipic acid as a product. Oxidation of cyclohexane with TS1 catalyst, for comparison, is less efficient and requires elevated temperatures.

DETAILED DESCRIPTION OF THE PREFERRED EMBODIMENTS

Cp$_2$CoOH as a structure directing agent clearly has a tendency to form cage type structures and appears to have a tendency to parallel the behavior of quinuclidine.

On the other hand, the high silica molecular sieves prepared using Cp*$_2$CoOH as the template appear to have a large pore, parallel channel system. Additionally, there appear to be only a limited number of high silica molecular sieve that crystallize with the Cp*$_2$CoOH template. This contrasts to the smaller Cp$_2$CoOH that facilitates the formation of several high silica phases. Furthermore, UTD-1 actually crystallizes in a fairly narrow window from the perspective of both time and template concentration.

High resolution electron microscopy of as synthesized, UTD-1 has revealed channels running parallel in one direction. The micropore volumes (cc/gm) determined from N$_2$, Ar and cyclohexane adsorption (0.113, 0.117 and 0.108 respectively) are also consistent with a channel type zeolite. Additionally, catalytic conversions, particularly the conversion of methanol to hydrocarbons with a narrow product distribution composed largely of higher molecular weight aromatics, is also consistent with a parallel dimensional channel type structure (Yuen et al, 1994). The incorporation of Al and B into the framework is expected to enhance the acidity and catalytic activity for such hydrocarbon conversions. Unhindered adsorption of cyclohexane (kinetic diameter 6A) and triethylamine (7.8A) is consistent with channel openings composed of 14 membered (based on the Si atoms) rings as well as the adsorption behavior of argon which is also consistent with the 14 membered ring apertures.

Freshly synthesized UTD-1 is bright yellow in color indicating the presence of the Cp*$_2$Co$^+$ template which has been confirmed spectroscopically. UTD-1 is thermally stable to calcination at >800° C. in air; however, the metal complex decomposes at ~370° C. to form a pale green-gray material. The arises from small cobalt oxide clusters adsorbed on the UTD-1 surface which can be removed by washing with HCl.

UTD-1 is a new zeolite with a 14 membered ring channel structure. An important issue is framework modification which includes the incorporation of aluminum and boron as well as reactive metal centers such as titanium and vanadium. The incorporation of titanium into the UTD-1 precursor gel dramatically modifies the synthesis such that after 2 days heating, which is normally the optimum crystallization time for UTD-1, only amorphous materials result. If, on the other hand, the same gel is heated for 6 days a crystalline product that appears isostructural with UTD-1, is produced. In contrast, the silicate or aluminosilicate gel forms the dense phase cristobalite after 3 days heating.

Figure 1:
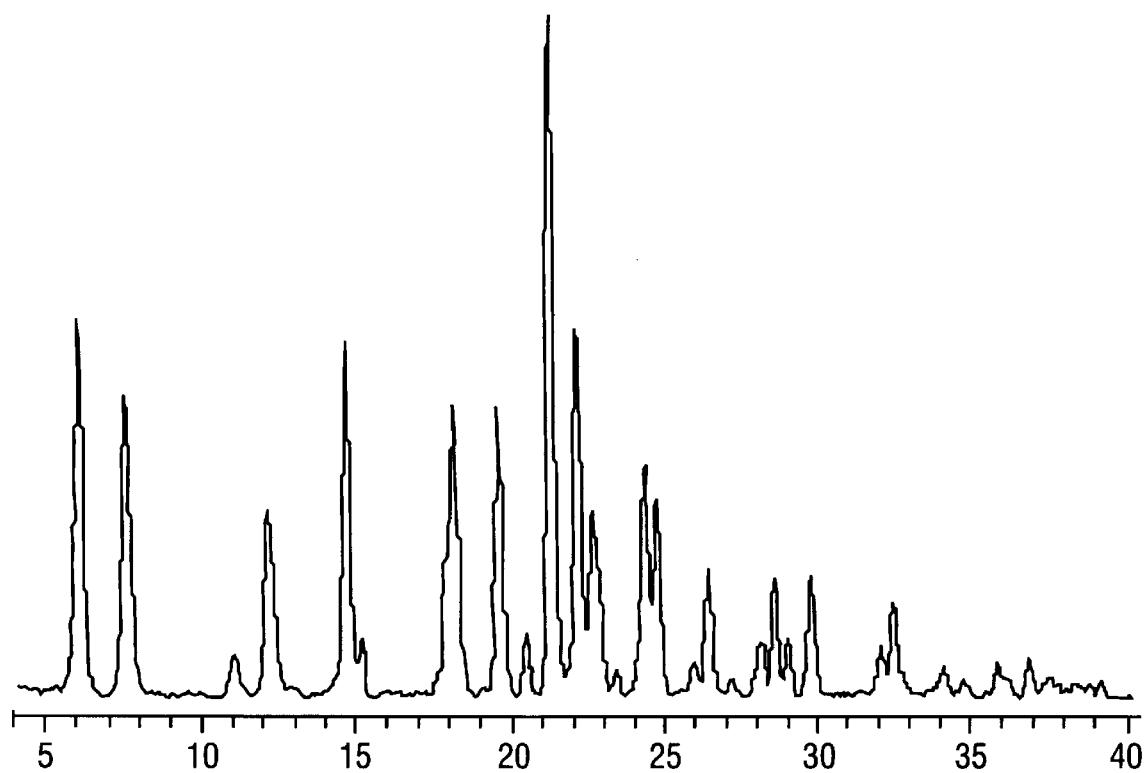
FIG. 1 shows the X-ray diffraction pattern for Ti-UTD-1 as synthesized or calcined
Figure 2:
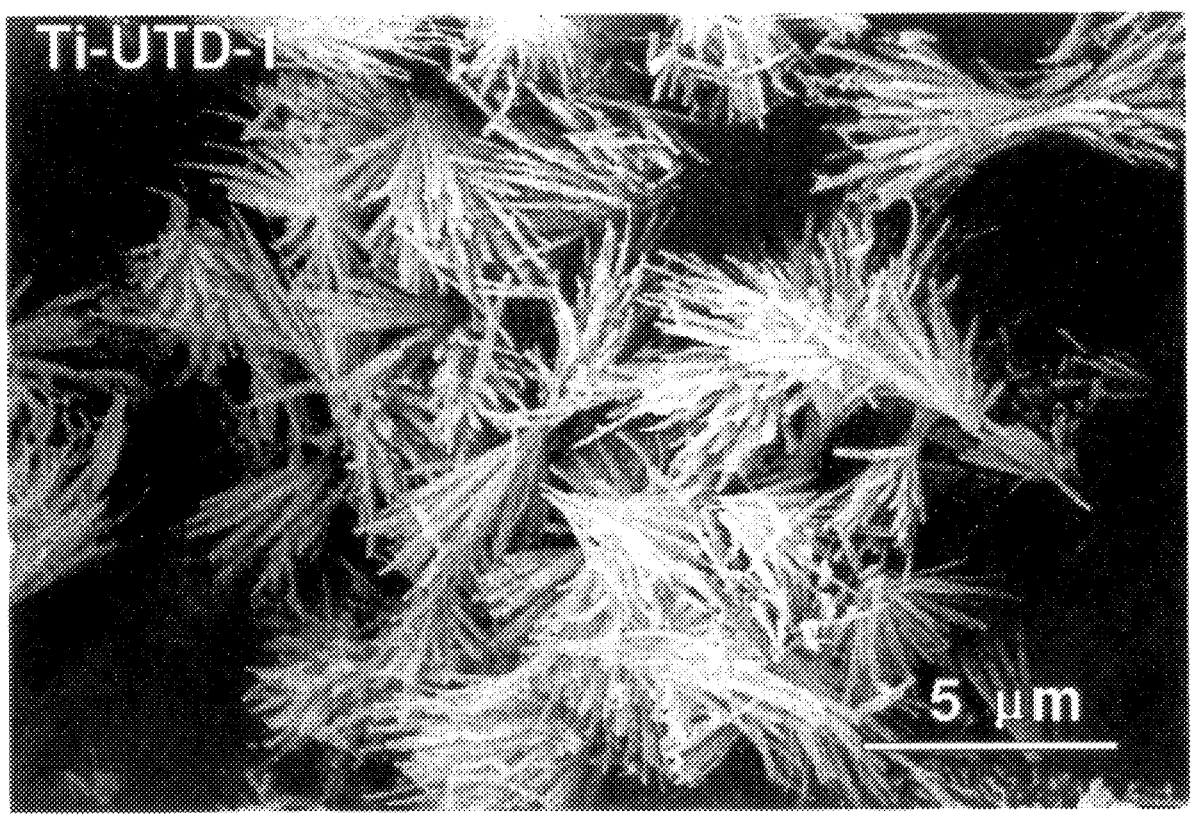
FIG. 2 is a scanning electron micrograph of Ti-UTD-1

The XRD pattern for Ti-UTD-1 is shown in FIG. 1 and is nearly the same as the all-silica UTD-1. Likewise, crystal morphologies of Ti-UTD-1 and UTD-1 are quite similar as shown in FIG. 2. The Ti-UTD-1 crystals are composed of bundles of needles which on average are considerably smaller than those observed for UTD-1. The SEM images also confirm the lack of impurity phases in this Ti-UTD-1 sample.

Figure 3:
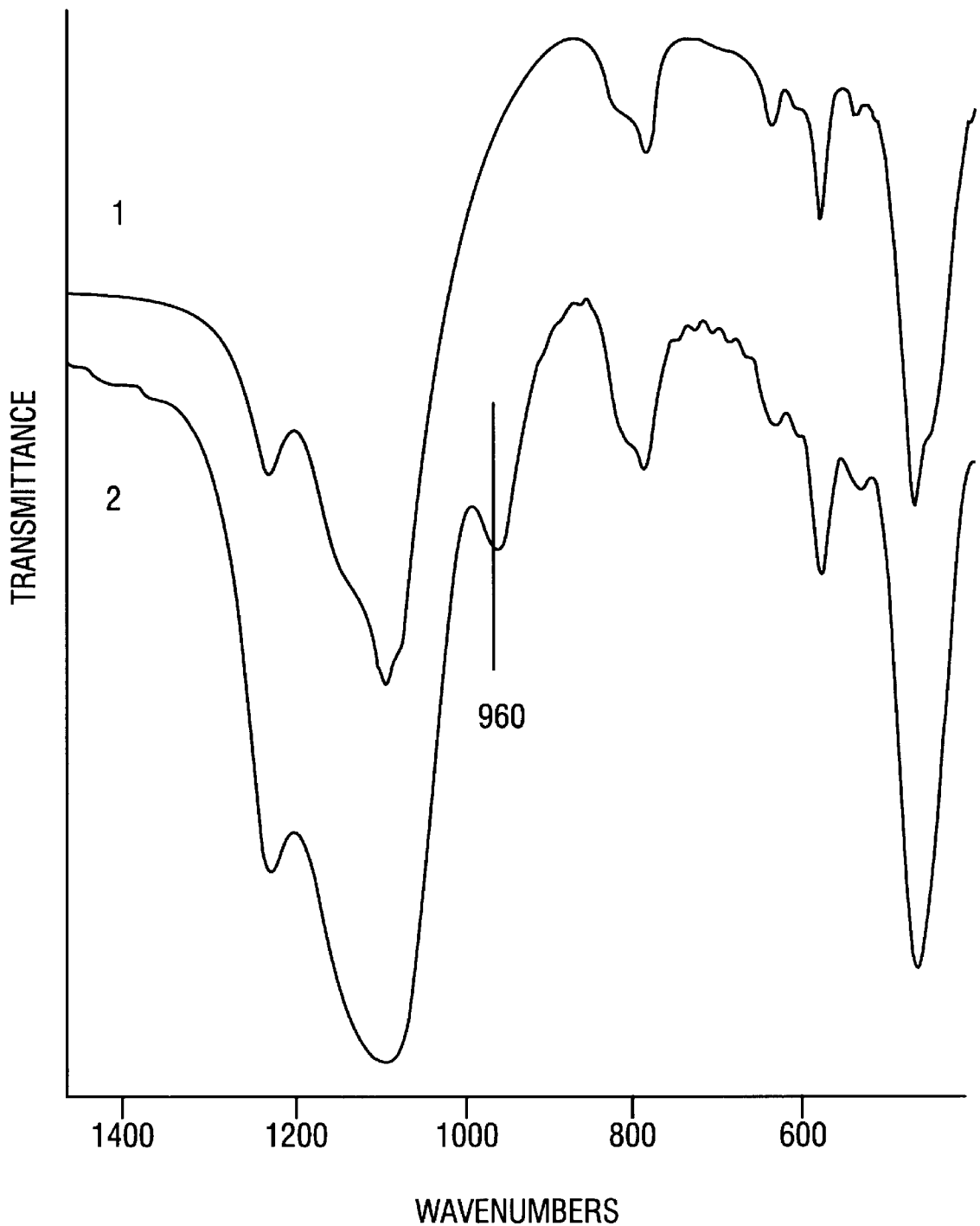
FIG. 3 shows the FT-IR spectra of calcined UTD-1 and Ti-UTD-1 recorded from KBr pellets

Elemental analysis of Ti-UTD-1 indicates 1–3.5 % Ti by weight. XRF analysis of the Ti-UTD-1 crystals indicates a fairly homogeneous distribution of Ti at a level consistent with the elemental analysis. Also the amount of cobalt incorporated (2.5%) is quite similar to the UTD-1 synthesis. Some evidence of the intrazeolite location of titanium is provided by IR spectroscopy. FIG. 3 shows the FT-IR spectra of UTD-1 and Ti-UTD-1 illustrating the structural similarity between the two phases. The most notable difference is a band at 960 cm$^{-1}$. This band is generally observed for titanosilicate molecular sieves and increases in intensity upon calcination. Corma et al. (1994) assigned this band to Si—O$^-$ defects due incorporation of titanium which transform to Si—OH upon calcination. These results indicate that titanium is incorporated into the UTD-1 structure.

Figure 4:
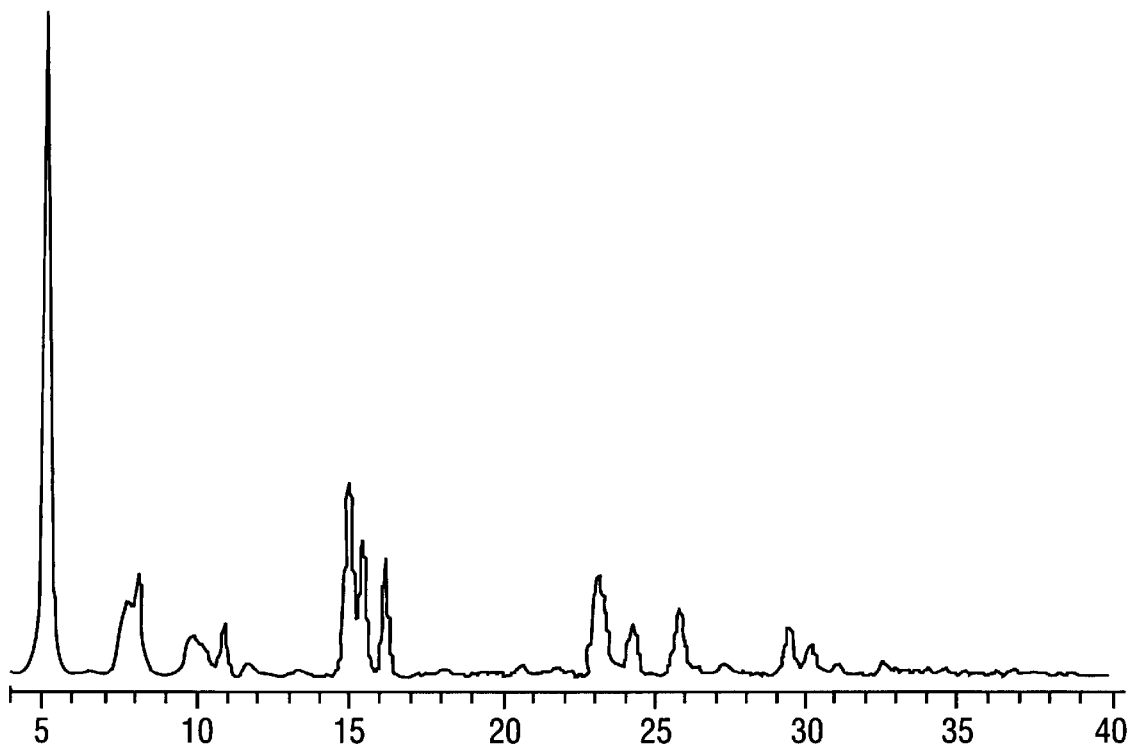
FIG. 4 shows the X-ray diffraction pattern for Ti-UTD-8

Care must be taken in the synthetic procedures because it is relatively easy to precipitate TiO$_2$ during gel preparation. On those occasions when the Ti-UTD-1 precursor gels were not homogeneous, an impurity phase (Ti-UTD-8) was typically observed. The x-ray diffraction pattern of a pure preparation is shown in FIG. 4.

Figure 5:
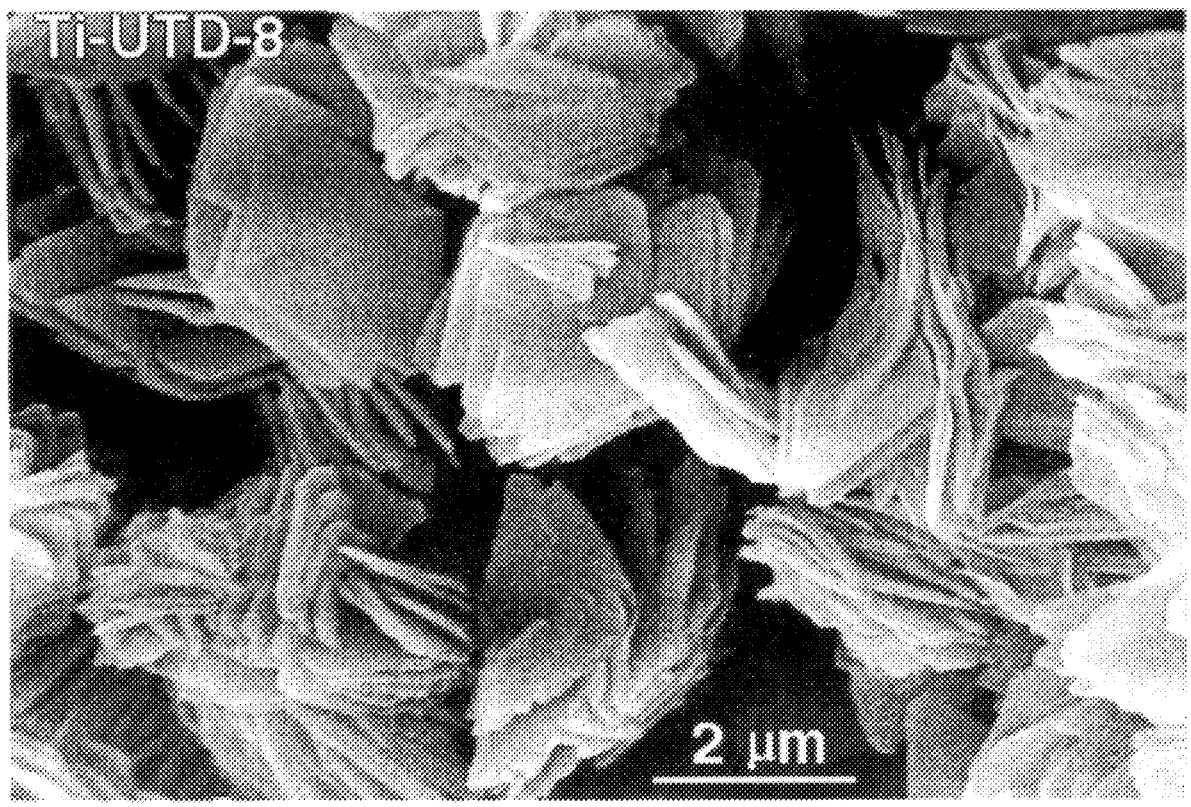
FIG. 5 is a scanning electron micrograph of Ti-UTD-8

Ti-UTD-8 appears to be a novel phase. This material is indicated to be a single phase as evidenced by the SEM shown in FIG. 5. XRF measurements also indicate a relatively high concentration of titanium (Si/Ti=4.5). In contrast to the UTD-1 structure, the Ti-UTD-8 structure collapses at ~370° C. which coincides with metal complex decomposition, making it difficult to measure meaningful adsorption data.

Cp*$_2$CoOH acts as a template for the synthesis of the large pore zeolite UTD-1 and for the titanium substituted analog, Ti-UTD-1. (Experiments using these molecular sieves as catalysts for the oxidation of alkanes using peroxides indicate that they are effective oxidation catalysts.) The results indicate that titanium modifies the gel chemistry and that other elements such as vanadium, aluminum and boron can also be incorporated into the structure.

Oxidation of cyclohexane was used as a model reaction for evaluating the catalytic activity of Ti-UTD-1. The reactions were run with Ti present at 3.5 % by weight and with t-butylhydroperoxide as the oxidant; however, analogous results are obtained with hydrogen peroxide or lesser loadings of Ti as well as with O$_2$(50psig). The large pore nature of Ti-UTD-1 allows the use of this bulky oxidant which provides an advantage over the medium pore TS-1. The oxidation of cyclohexane at room temperature over Ti-UTD-1 results in the formation of cyclohexanone as the major product with lesser amounts of cyclohexanol and adipic acid. The formation of adipic acid was confirmed by GC/MS as well as by IR, NMR and XRD.

Comparable activity by titanosilicates do not seem to be known, especially the formation of adipic acid at room temperature. In general, the oxidation of cycloalkanes appears to be a difficult reaction over catalysts such as TS-1. For example, for a TS-1 catalyzed oxidation of cyclohexane in acetone at 100° C. only 44.7 turnovers (based on one+ol products) were registered after 24 hours (Schuchardt, et al, 1994), although this is an improvement over reactions in alcohol solvents such as methanol where only 12.6 turnovers are noted under the same conditions. The turnovers in the presently disclosed catalytic reaction based on ketone and alcohol are comparable; however, the ketone is converted to adipic acid and other products in trace amounts, indicated in Scheme I.

Scheme 1

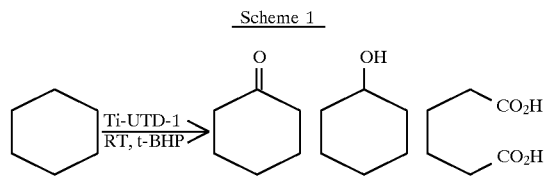

Figure 6:
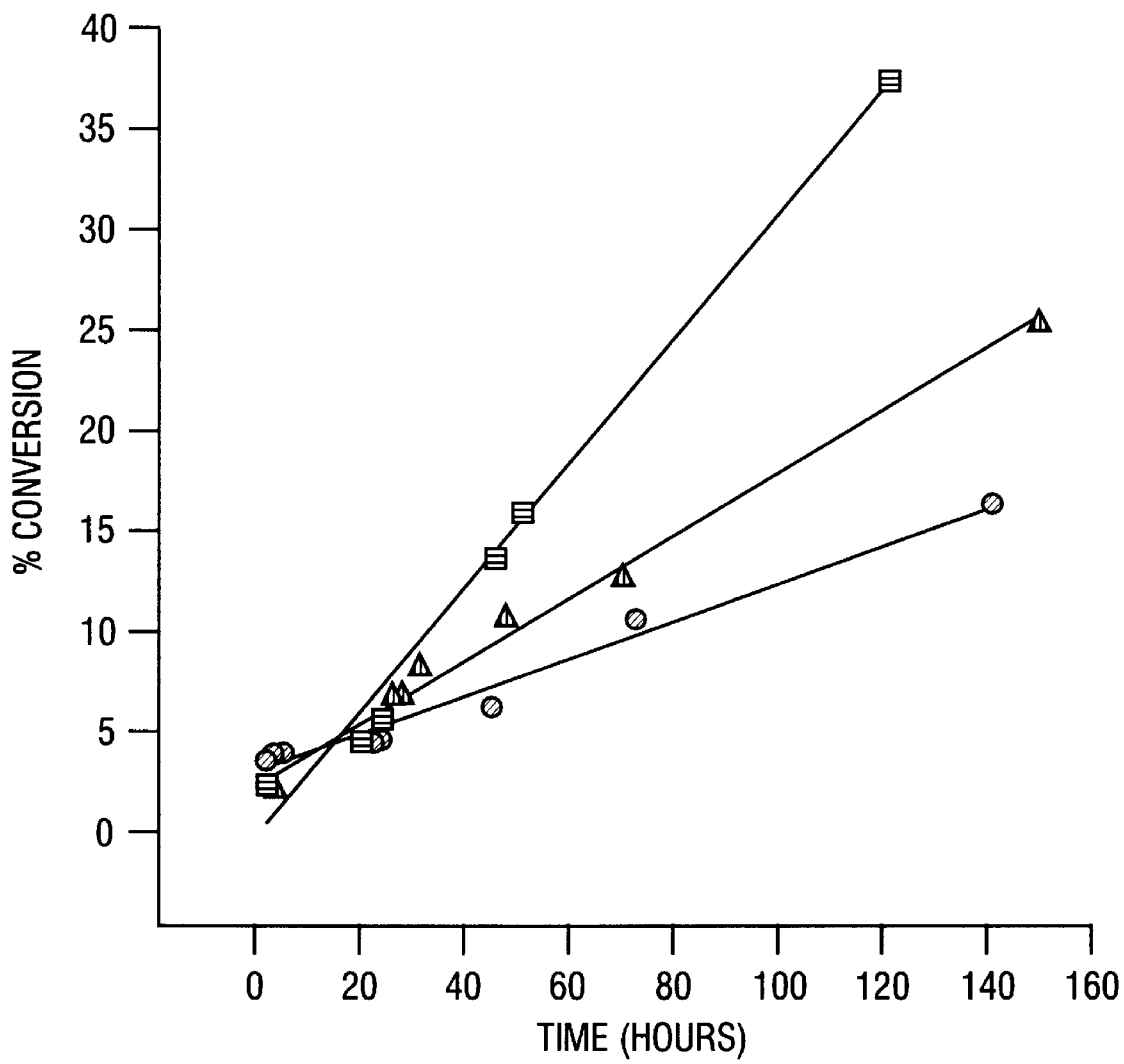
FIG. 6 shows a plot of cyclohexane conversion at room temperature versus time catalyzed by calcined UTD-1, Ti-UTD-1 (containing cobalt) and cobalt-free Ti-UTD-1

In evaluating this reaction it was important to determine if trace amounts of cobalt oxide generated from the decomposed template influenced the reaction, since commercial cyclohexane oxidation involves soluble cobalt ions. The activities of calcined UTD-1 without titanium, Ti-UTD-1 containing cobalt and cobalt-free Ti-UTD-1 were compared. FIG. 6 shows a plot of cyclohexane conversion at room temperature versus time for the three different molecular sieves. The lowest activity is observed for the all-silica UTD-1 that contains the cobalt oxide clusters. However, the calcined Ti-UTD-1 that contains approximately the same amount of cobalt (~3 % by weight) is clearly more active.

Cobalt oxide clusters can be removed from the Ti-UTD-1 catalysts. Although supported cobalt species are catalytically active, trace amounts of cobalt cannot account for the observed activity with Ti-UTD-1, since the presence of cobalt appears to hinder the activity of the titanosilicate. Increasing the temperature to 60° C. increases the activity such that complete conversion can be achieved over the same time frames in FIG. 6. There do not appear to be any dramatic changes in peroxide efficiency.

The Ti-UTD-1 molecular sieves are effective in decomposing peroxides. For example, the addition of Ti-UTD-1 to a 70% aqueous H$_2$O$_2$ solution immediately generates enough heat for the solution to begin to boil. The reaction with t-BHP is not as dramatic, although over 85% conversion was observed after 3 hours at 60° C. Peroxide efficiency appears to be decreased when acetone is employed as solvent. Significant solvent effects have been noted before in the case of TS-1 catalyzed oxidations (Schuchardt, et al, 1994; Tatsumi et al, 1994). In the H$_2$O$_2$ based oxidations there is a phase separation between the organic and the water layer. Polar solvents promote the reaction by assisting in phase transfer. In non-aqueous media employing t-BHP, there appears to be competitive adsorption in Ti-UTD-1.

Figure 7:
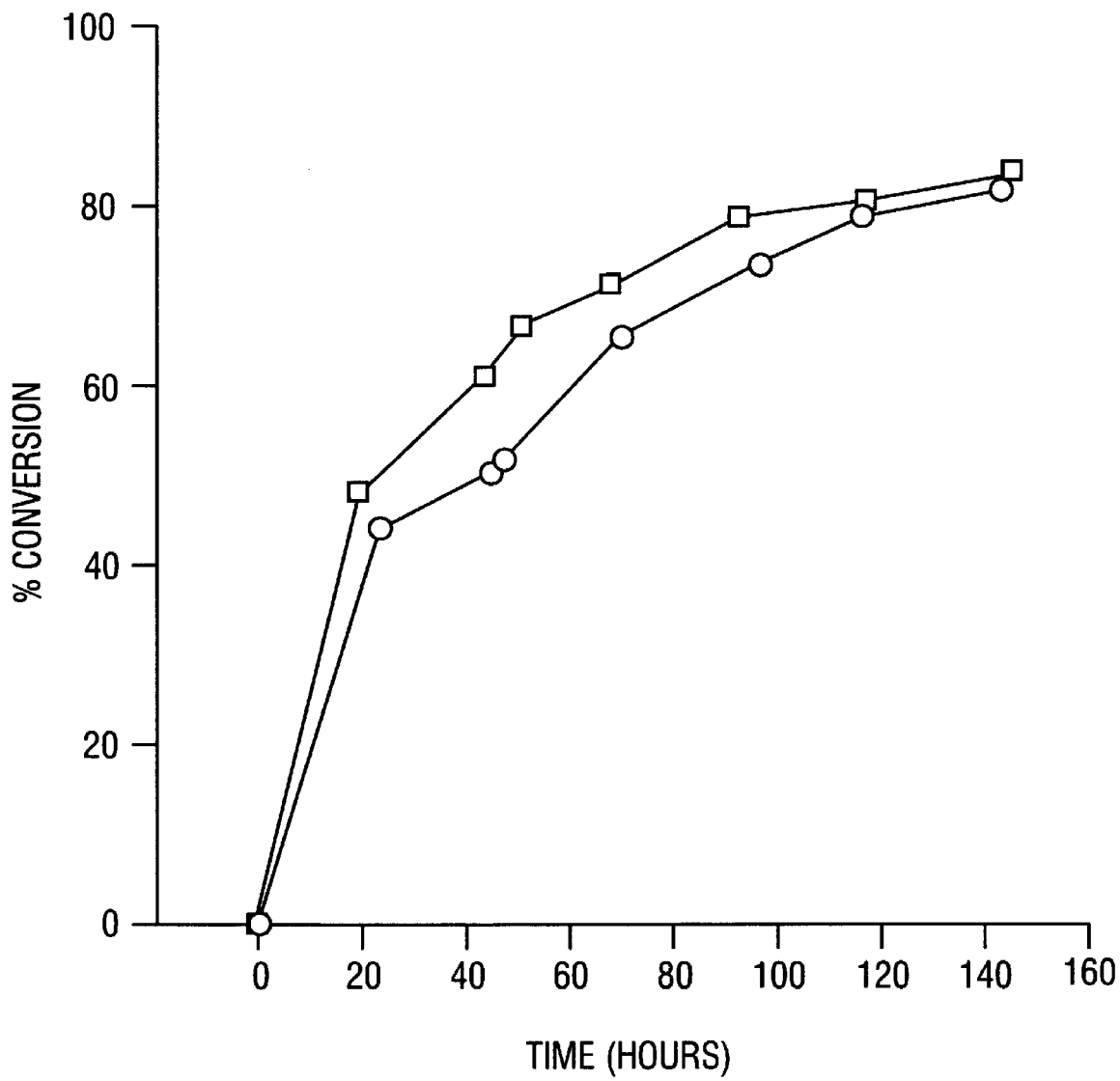
FIG. 7 is a plot of cyclohexane conversion at 60° C. versus time catalyzed by calcined UTD-1 and Ti-UTD-1 (containing cobalt)

The oxidation of cyclohexane in the absence of solvent was studied. Results are shown in FIG. 7 which is a plot of cyclohexane conversion at 60° C. versus time indicating higher conversions at shorter times. Additionally, the peroxide efficiency improves such that after one day there is ~50% conversion of the cyclohexane; or ~60% conversion employing t-BHP. The conversion to adipic acid also increases to the point that it becomes the major product.

Figure 8:
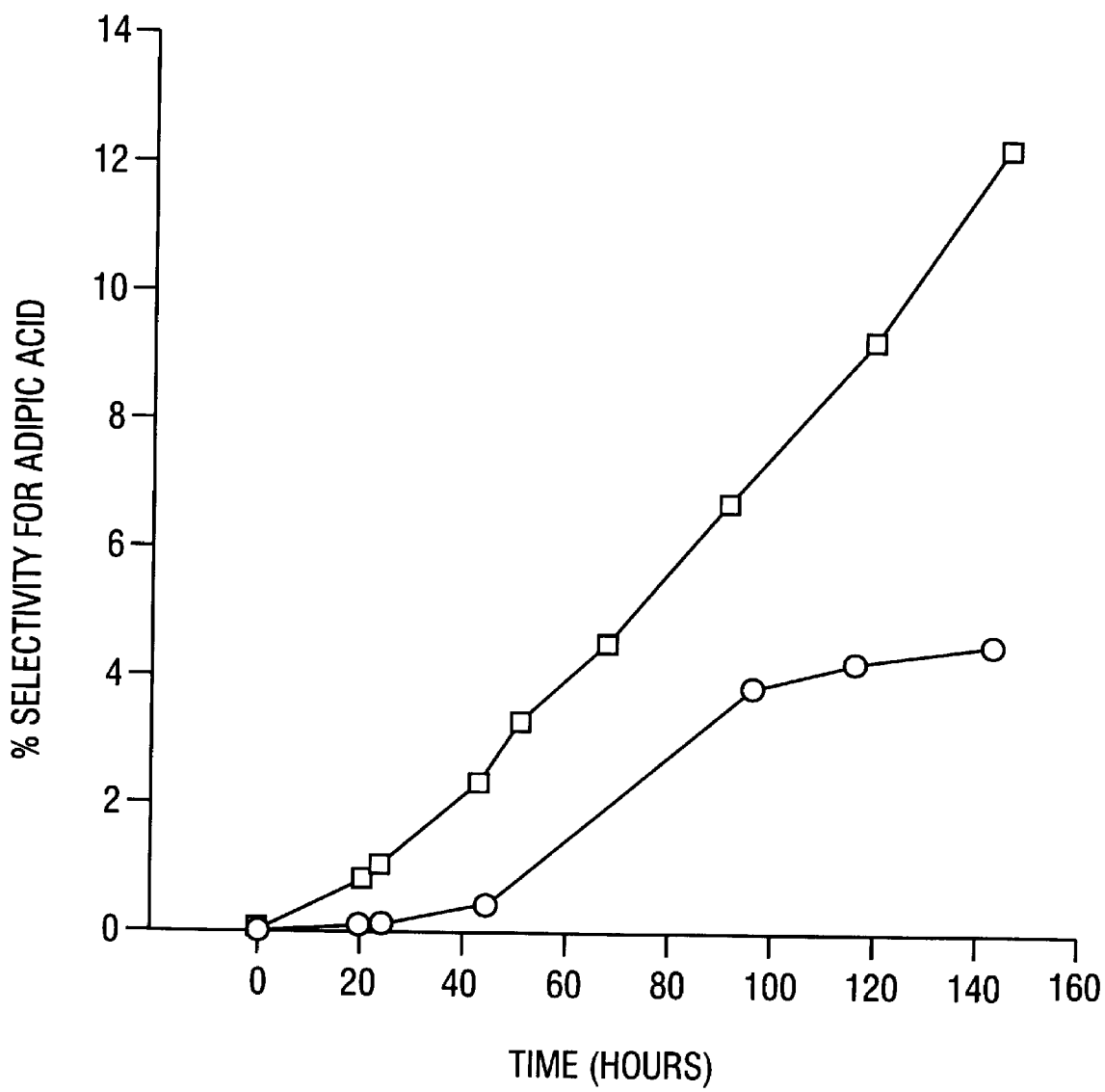
FIG. 8 shows a plot of percent selectivity for adipic acid versus time for the Ti-UTD-1 and UTD-1 containing cobalt catalysts.

The selectivity of the reaction varies with time due to the involvement of a series of sequential oxidations. For example, in acetone the initial products observed in nearly equal quantities are the ketone and alcohol. Cyclohexanol is oxidized to cyclohexanone such that the one/ol ratio increases with time. Similarly, the cyclohexanone is oxidized to adipic acid. In the absence of solvent, the selectivity towards adipic acid increases. FIG. 8 shows a plot of % selectivity for adipic acid versus time for the Ti-UTD-1 and UTD-1 (with cobalt) catalysts. After one week and ~85% conversion of cyclohexane, approximately 12% of the product is adipic acid. At ~25% yield of cyclohexanone the amount of ketone decreases as the amount of adipic acid increases. At 98% conversion of the cyclohexane, ~50% of the product is adipic acid.

These results show that titanium can be incorporated into the UTD-1 structure at levels as high as 3.5% by weight. Both the extraframework cobalt derived from the template and the framework titanium are effective oxidation catalysts. The conversion of cyclohexane to adipic acid under relatively mild conditions indicates the potential of these materials as oxidation catalysts.

While certain of the compositions have been characterized by recitation of a particular x-ray diffraction pattern, it will be understood by those skilled in the art that some variation in pattern may be expected with any preparation and that certain lines may be shifted or weaker lines not apparent. Thus such variations are contemplated to be within the scope of the invention and would be expected to have substantially the same properties providing substantially the same results as those particular forms described and claimed.

The following examples are included to demonstrate preferred embodiments of the invention. It should be appreciated by those of skill in the art that the compositions and reactions discovered by the inventors and shown in the examples represent embodiments discovered by the inventors to function well in the practice of the invention, and thus can be considered to constitute preferred modes for its practice; however, those of skill in the art should, in light of the present discussion, appreciate that many changes can be made in the specific embodiments which are disclosed and still obtain a like or similar result without departing from the spirit and scope of the invention.

EXAMPLE 1

Ti-UTD-1 and UTD-8 were prepared as shown in the following examples. The UTD-1 has been previously described in U.S. Pat. No. 5,489,424, 1996, the entire specification of which is herein incorporated by reference.
Methods The synthesis of UTD-1 is described in Balkus et al (1995) and Balkus and Gabrielov (1995). All reagents were used as purchased unless indicated otherwise. Electronic spectra of zeolites were obtained from samples prepared as nujol mulls between quartz plates using a Hitachi U-2000 UV-2025 FT-IR spectrophotometer. Mid-IR spectra were obtained from KBr pellets using a Mattson Scintag XDS 2000 diffractometer using $CaF_2$ as an internal standard. Scanning electron micrographs were obtained using a Philips XL30 SEM equipped with Philips PV8500 EDAX spectrometer. Elemental analyses were performed by Galbraith Laboratories, Knoxville, Tenn.

EXAMPLE 2

The following are examples of Al-UTD-1 Preparations
Preparation of Al-UTD-1 (A)

A gel having a molar ratio of $SiO_2$ : $Al_2O_3$ : $Na_2O$ : $Cp*_2CoOH$ : $H_2O$=1: 0.00037 : 0.045 : 0.1 : 56 was prepared in a 50 mL polypropylene beaker at room temperature. 0.06 grams of NaOH were dissolved in 15 mL of deionized water. Then 2.41 grams of a 24% decamethylcobalticinium hydroxide ($Cp*_2CoOH$) solution in water were added with stirring. 1 gram of fumed silica was added in 4 portions over a period of 20 minutes. The gel was stirred for additional 15 min. A sodium aluminate solution was prepared by combining 0.4 grams of aluminum isopropoxide, 0.11 grams of NaOH and 4 grams of deionized water. 0.025 grams of the solution were added to the gel. The beaker was covered and the gel was aged with stirring for 1 hour until a homogeneous gel was obtained. The gel was then transferred into a 23 mL Teflon-lined pressure reactor that was subsequently placed in an oven having a constant temperature of 175° C. After 2 days heating under static conditions, the mixture was cooled to RT, diluted with 250 mL of deionized water and suction filtered through a nitrocellulose membrane (2 μm). The yellow crystals were collected, mixed with 250 mL of water, suction filtered and dried at 90° C. for 15 hours. Elemental analysis indicated 40.0% Si, 2.6% Co, 0.04% Al by weight.

TABLE 1

X-Ray Diffraction Pattern for Al-UTD-1

| Interplanar d-spacing (Å) | Relative intensity | Interplanar d-spacing (Å) | Relative intensity |
|---|---|---|---|
| 14.72 | s | 3.82 | vw |
| 11.76 | m | 3.67 | m |
| 8.07 | vw | 3.61 | w |
| 7.33 | w | 3.45 | vw |
| 6.06 | s | 3.39 | w |
| 5.88 | w | 3.20 | vs |
| 4.96 | w | 3.13 | w |
| 4.90 | m | 3.09 | vw |
| 4.56 | m | 3.01 | w |
| 4.36 | w | 2.80 | vw |
| 4.32 | vw | 2.76 | w |
| 4.19 | vs | 2.64 | vw |
| 4.03 | m | 2.44 | vw |
| 3.94 | w | 2.40 | vw |

Intensity scale is: vw = 0–10%, w = 10–40%, m = 40–60%, s = 60–80%, vs = 80–100%

TABLE 2

X-Ray Diffraction Pattern for Al-UTD-1 Calcined at 500° C.

| Interplanar d-spacing (Å) | Relative intensity | Interplanar d-spacing (Å) | Relative intensity |
|---|---|---|---|
| 14.61 | vs | 3.84 | vw |
| 11.51 | m | 3.66 | w |
| 9.46 | vw | 3.56 | w |
| 6.09 | w | 3.40 | w |
| 4.88 | w | 3.19 | vw |
| 4.48 | w | 3.16 | vw |
| 4.38 | vw | 3.06 | vw |
| 4.20 | m | 2.98 | vw |
| 4.09 | w | 2.77 | vw |
| 3.94 | vw | | |

Preparation of Al-UTD-1 (B)

A gel having a molar ratio of $SiO_2$: $Al_2O_3$ : $Na_2O$: $CP*_2CoOH$ : $H_2O$=1: 0.0013 0.045 : 0.1: 56 was prepared in a 50 mL polypropylene beaker at room temperature. 0.06 grams of NaOH were dissolved in 15 mL of deionized water. Then 2.41 grams of a 24% decamethylcobalticinium hydroxide ($CP*_2CoOH$) solution in water were added with stirring. 1 gram of fumed silica was added in 4 portions over a period of 20 minutes. The gel was stirred for additional 15 min. 0.09 grams of the sodium aluminate solution, described in Example 1, were added to the gel. The beaker was covered and the gel was aged with stirring for 1 hour until homogeneous gel was obtained. The gel was then transferred to a 23 mL Teflon-lined pressure reactor that was subsequently placed in an oven having a constant temperature of 175° C.

After 2 days heating under static conditions, the mixture was cooled to RT, diluted with 250 mL of deionized water and suction filtered through a nitrocellulose membrane (2 μm). The solid residue was collected, mixed with 250 mL of water, suction filtered and dried at 90° C. for 15 hours. Elemental analysis indicated 40.1% Si, 2.2% Co, 0.05% Al by weight.

TABLE 3

X-Ray Diffraction Pattern for Al-UTD-1

| Interplanar d-spacing (Å) | Relative intensity | Interplanar d-spacing (Å) | Relative intensity |
|---|---|---|---|
| 14.73 | m | 3.82 | vw |
| 11.77 | m | 3.67 | m |
| 8.08 | vw | 3.61 | w |
| 7.33 | w | 3.45 | vw |
| 6.06 | s | 3.39 | w |
| 5.88 | w | 3.20 | vw |
| 4.96 | w | 3.13 | w |
| 4.90 | m | 3.09 | vw |
| 4.56 | m | 3.01 | w |
| 4.36 | w | 2.80 | vw |
| 4.32 | vw | 2.76 | w |
| 4.19 | vs | 2.64 | vw |
| 4.10* | w | 2.50* | w |
| 4.03 | m | 2.44 | vw |
| 3.94 | w | 2.40 | vw |

Intensity scale is: vw = 0–10%, w = 10–40%, m = 40–60%, s = 60–80%, vs = 80–100%
(*) = impurity peaks

TABLE 4

X-Ray Diffraction Pattern for Al-UTD-1 Calcinated at 500° C.

| Interplanar d-spacing (Å) | Relative intensity | Interplanar d-spacing (Å) | Relative intensity |
|---|---|---|---|
| 14.61 | vs | 3.84 | vw |
| 11.51 | m | 3.66 | w |
| 9.46 | vw | 3.56 | w |
| 6.09 | w | 3.40 | w |
| 4.88 | w | 3.19 | vw |
| 4.48 | w | 3.16 | vw |
| 4.38 | vw | 3.06 | vw |
| 4.20 | s | 2.98 | vw |
| 4.09 | w | 2.77 | vw |
| 4.05* | w | 2.72* | v |
| 3.94 | vw | | |

(*) = impurity peaks

EXAMPLE 3

The following illustrates several examples of the preparation of Ti-UTD-1.

Preparation of Ti-UTD-1 (A)

2.81 grams of tetraethylorthosilicate (TEOS) were mixed with 3.46 grams of an aqueous 19% $Cp^*_2CoOH$ solution followed by 2.35 mL of deionized water. The mixture was cooled to 0° C. using an ice bath and 0.2 grams of titanium ethoxide (20% Ti) solution were carefully added to the mixture with stirring. The mixture was gradually heated to 60° C. (1 deg min$^{-1}$) and stirred until a transparent pale-brown solution was obtained. Then, 7 mL of deionized water were carefully added to the solution which was then heated to 80° C. and stirred for 1 hour using a water bath. After cooling to RT, the transparent gel having a molar ratio of $SiO_2 : TiO_2 : Cp^*_2CoOH : H_2O$ =1: 0.062 : 0.14 : 50 was transferred to a 23 mL Teflon-lined autoclave that was placed in an oven at 175° C. for 6 days. The mixture was then cooled to RT. The yellow crystals were isolated by suction filtration, washed with deionized water and dried at 90° C. for 15 hours. Elemental analysis indicated 33.7% Si, 3.4% Ti, 3.1% Co by weight.

TABLE 5

X-Ray Diffraction Pattern for Ti-UTD-1

| Interplanar d-spacing (Å) | Relative intensity | Interplanar d-spacing (Å) | Relative intensity |
|---|---|---|---|
| 14.73 | s | 3.92 | w |
| 11.78 | m | 3.67 | s |
| 7.33 | m | 3.62 | m |
| 6.06 | vs | 3.39 | w |
| 5.89 | w | 3.20 | vw |
| 4.98 | m–w | 3.14 | w |
| 4.90 | s | 3.10 | w |
| 4.56 | m | 3.01 | w |
| 4.36 | m–w | 2.80 | w |
| 4.21 | vs | 2.77 | w |
| 4.04 | m | 2.45 | vw |
| 3.96 | w | | |

TABLE 6

X-Ray Diffraction Pattern for Ti-UTD-1 Calcinated at 500° C.

| Interplanar d-spacing (Å) | Relative intensity | Interplanar d-spacing (Å) | Relative intensity |
|---|---|---|---|
| 14.70 | vs | 3.73 | vw |
| 11.57 | m | 3.66 | w |
| 9.46 | vw | 3.56 | vw |
| 6.10 | w | 3.40 | vw |
| 4.88 | w | 3.19 | vw |
| 4.48 | w | 3.16 | vw |
| 4.39 | vw | 3.08 | vw |
| 4.22 | w | 3.05 | vw |
| 4.05 | vw | 2.99 | vw |
| 3.97 | vw | 2.77 | vw |
| 3.84 | vw | | |

Preparation of Ti-UTD-1 (B)

16.87 grams of tetraethylorthosilicate (TEOS) were mixed with 20.76 grams of an aqueous 19% $Cp^*_2CoOH$ solution. The mixture was cooled to 0C and 1.2 grams of titanium ethoxide (20% Ti) solution were carefully added to the mixture with stirring. The mixture was gradually heated up to 60° C. (1 deg min~$^{-1}$) and stirred for ~1 hour until a transparent pale-brown solution was obtained. Then, 2 mL of deionized water were added to the solution which was then heated to 80° C. and stirred for 1.5 hours. After adding 52 mL of deionized water (dropwise) to the solution the final gel had a molar ratio of $SiO_2 : TiO_2 : Cp^*_2CoOH\ H_2O$=1: 0.062: 0.14 : 49. The transparent gel was then transferred to a Teflon-lined autoclave and heated to 175° C. under static conditions for 6 days. The crystallization mixture was then cooled to room temperature. The yellow crystals were isolated by suction filtration, washed with deionized water and dried at 90° C. for 15 hours. Elemental analysis indicated 33.1% Si, 3.5% Ti, 2.8% Co by weight.

TABLE 7

X-Ray Diffraction Pattern for Ti-UTD-1

| Interplanar d-spacing (Å) | Relative intensity | Interplanar d-spacing (Å) | Relative intensity |
|---|---|---|---|
| 14.73 | s | 3.95 | w |
| 13.74 | w (sh) | 3.67 | m |
| 11.81 | m | 3.62 | m |

TABLE 7-continued

X-Ray Diffraction Pattern for Ti-UTD-1

| Interplanar d-spacing (Å) | Relative intensity | Interplanar d-spacing (Å) | Relative intensity |
|---|---|---|---|
| 7.33 | m | 3.39 | w |
| 6.87 | vw | 3.20 | vw |
| 6.07 | s | 3.14 | w |
| 5.91 | w | 3.09 | w |
| 4.90 | s | 3.01 | w |
| 4.57 | m | 2.81 | w |
| 4.37 | w | 2.77 | w |
| 4.21 | vs | 2.50 | vw |
| 4.04 | m | | |

TABLE 8

X-Ray Diffraction Pattern for Ti-UTD-1 Calcinated at 500° C.

| Interplanar d-spacing (Å) | Relative intensity | Interplanar d-spacing (Å) | Relative intensity |
|---|---|---|---|
| 14.63 | vs | 3.77 | vw |
| 11.54 | m | 3.66 | w |
| 9.48 | vw | 3.56 | vw |
| 6.10 | vw | 3.40 | vw |
| 4.89 | w | 3.19 | vw |
| 4.48 | w | 3.16 | vw |
| 4.39 | vw | 3.07 | vw |
| 4.22 | m | 3.06 | vw |
| 4.06 | vw | 2.98 | vw |
| 3.96 | vw | 2.77 | vw |
| 3.85 | vw | | |

Preparation of Ti-UTD-1 (C)

The titanosilicate Ti-UTD-1 was prepared by first combining 6 mL of deionized water with 3.37 grams of an aqueous 19.8% Cp*$_2$CoOH solution and 0.027 grams of NaOH. The template solution was mixed with 0.81 grams of fumed silica and stirred at room temperature for one hour. Then 0.065 grams of titanium ethoxide (20% Ti) solution were added dropwise to the silicate solution with stirring. The gel was stirred at 80° C. for 2 hours during which time the gel became more viscous and almost transparent in appearance. At that point 3 mL of water were added. The resulting titanosilicate gel had a molar ratio of SiO$_2$ : TiO$_2$: Cp*$_2$CoOH : Na$_2$O: H$_2$O=1: 0.02 : 0.14 : 0.025 : 48. The gel was transferred to a 23 mL Teflon-lined autoclave and then heated under static conditions at 175° C. for 6 days. The crystallization mixture was then cooled to room temperature. The yellow Ti-UTD-1 was isolated by suction filtration, washed with deionized water and dried at 90° C. for 15 hours. Elemental analysis indicated 37.2% Si, 0.94% Ti, 2.46% Co by weight.

TABLE 9

X-Ray Diffraction Pattern for Ti-UTD-1

| Interplanar d-spacing (Å) | Relative intensity | Interplanar d-spacing (Å) | Relative intensity |
|---|---|---|---|
| 14.70 | m | 3.95 | w |
| 11.76 | m | 3.92 | w |
| 8.07 | vw | 3.67 | m |
| 7.32 | w | 3.62 | m |
| 6.06 | m | 3.39 | w |
| 5.88 | vw | 3.20 | vw |
| 4.98 | w | 3.14 | w |
| 4.90 | m | 3.09 | w |
| 4.56 | m | 3.01 | w |
| 4.36 | w | 2.80 | w |
| 4.20 | vs | 2.77 | w |
| 4.03 | m | 2.44 | vw |

TABLE 10

X-Ray Diffraction Pattern for Ti-UTD-1 Calcinated at 500° C.

| Interplanar d-spacing (Å) | Relative intensity | Interplanar d-spacing (Å) | Relative intensity |
|---|---|---|---|
| 14.63 | vs | 3.66 | w |
| 11.54 | s | 3.56 | vw |
| 9.48 | vw | 3.40 | vw |
| 6.10 | w | 3.19 | vw |
| 4.88 | w | 3.16 | vw |
| 4.48 | w | 3.06 | vw |
| 4.39 | vw | 3.06 | vw |
| 4.21 | m | 2.99 | vw |
| 4.05 | w | 2.77 | vw |
| 3.96 | vw | 2.72 | vw |
| 3.84 | vw | 2.46 | vw |
| 3.74 | vw | 2.44 | vw |

Preparation of Ti-UTD-1 (D)

2.81 grams of tetraethylorthosilicate (TEOS) were mixed with 3.46 grams of an aqueous 19% Cp*$_2$CoOH solution followed by 2.35 mL of deionized water. The mixture was cooled to 0° C. and 0.1 grams of titanium ethoxide (20% Ti) solution were added to the mixture with stirring. The mixture was gradually heated to 60° C. (1 deg min$^{-1}$) and stirred until a transparent pale-brown solution was obtained. Then 7 mL of deionized water were added to the solution which was subsequently heated to 80° C. with stirring for 1 hour. After cooling to RT, the transparent gel having a molar ratio of SiO$_2$ : TiO$_2$ : CP*$_2$CoOH : H$_2$O=1: 0.031: 0.14 : 50 was transferred to a 23 mL Teflon-lined autoclave that was heated at 175° C. for 6 days. The mixture was cooled to RT and the yellow crystals were isolated by suction filtration, washed with deionized water and dried at 90° C. for 15 hours. Elemental analysis indicated 36.3% Si, 1.6% Ti, 3.2% Co by weight.

TABLE 11

X-Ray Diffraction Pattern for Ti-UTD-1

| Interplanar d-spacing (Å) | Relative intensity | Interplanar d-spacing (Å) | Relative intensity |
|---|---|---|---|
| 14.74 | vs | 3.92 | w |
| 11.79 | s | 3.67 | s |
| 7.33 | m | 3.62 | m |
| 6.06 | vs | 3.39 | w |
| 5.89 | w | 3.20 | vw |
| 4.98 | w | 3.14 | w |
| 4.90 | vs | 3.09 | w |
| 4.56 | s | 3.01 | w |
| 4.37 | w | 2.80 | w |
| 4.21 | vs | 2.77 | w |
| 4.44 | m | 2.45 | vw |
| 3.95 | w | | |

TABLE 12

X-Ray Diffraction Pattern for Ti-UTD-1 Calcinated at 500° C.

| Interplanar d-spacing (Å) | Relative intensity | Interplanar d-spacing (Å) | Relative intensity |
|---|---|---|---|
| 14.66 | vs | 3.73 | vw |
| 11.55 | m | 3.66 | w |
| 9.48 | vw | 3.56 | vw |
| 6.10 | w | 3.40 | vw |
| 4.89 | w | 3.19 | vw |
| 4.48 | w | 3.16 | vw |
| 4.39 | vw | 3.07 | vw |
| 4.22 | w | 3.05 | vw |
| 4.05 | vw | 2.98 | vw |
| 3.96 | vw | 2.77 | vw |
| 3.86 | vw | | |

Ti-UTD-1 Synthesis (E)

The titanosilicate Ti-UTD-1 was prepared by first combining 3.37 grams of a 19.8% by weight aqueous solution of Cp*$_2$CoOH with 9 mL of deionized water and 0.027 grams of NaOH. The template solution was mixed with 0.81 grams of fumed silica and stirred at room temperature for one hour. Then 0.065 grams of a titanium ethoxide (20% Ti) solution (Aldrich) were added dropwise to the silicate solution with stirring. The gel was stirred at 80° C. for 2 hours during which time the gel became more viscous and transparent in appearance. At this point three additional milliliters of deionized water were added. The resulting titanosilicate gel had a molar ratio of SiO$_2$: TiO$_2$: Cp*$_2$CoOH: Na$_2$O: H$_2$O=1: 0.02: 0.14 : 0.025: 50. The gel was transferred to a 23 mL Teflon-lined autoclave and then heated under static conditions at 175° C. for 6 days. The crystallization mixture was cooled to room temperature, then the yellow Ti-UTD-1 was isolated by suction filtration, washed with deionized water and dried at 90° C. overnight.

EXAMPLE 4

Ti-UDT-8 was prepared in a manner similar to that employed for the preparation of Ti-UDT-1.

Preparation of TI-UTD-8

The titanosilicate Ti-UTD-8 was prepared by combining 9.82 grams of a 13.6% Cp*$_2$CoOH aqueous solution with 11 mL of deionized water, 0.108 grams of NaOH and 1.62 grams of fumed silica. The silicate gel was stirred for one hour at room temperature. Then 0.216 grams of the titanium ethoxide solution (20% Ti) were added dropwise to the mixture with stirring. The gel was covered and stirred for one hour at room temperature followed by additional stirring at 50° C. for three hours. The resulting opaque gel had a molar ratio of SiO$_2$ : TiO$_2$: Cp*$_2$CoOH: Na$_2$O : H$_2$O=1: 0.033 : 0.14 : 0.05 : 40. The gel was transferred to a Teflon-lined autoclave and heated under static conditions at 175° C. for 6 days. The crystallization mixture was cooled to room temperature and the liquid was decanted from the yellow solid on the bottom of the reactor. The Ti-UTD-8 was washed with copious amounts of deionized water and dried at room temperature for 24 hours. Elemental analysis indicated 22.1% Si, 9.3% Ti, 3.9% Co by weight.

TABLB 13

X-Ray Diffraction Pattern for Ti-UTD-8

| Interplanar d-spacing (Å) | Relative intensity | Interplanar d-spacing (Å) | Relative intensity |
|---|---|---|---|
| 17.40 | vs | 3.80 | w |
| 11.50 | vw | 3.75 | vw |
| 11.05 | w | 3.66 | w |
| 8.99 | vw | 3.46 | w |
| 8.84 | vw | 3.03 | vw |
| 8.70 | vw | 3.03 | vw |
| 8.20 | vw | 3.01 | vw |
| 7.66 | vw | 2.97 | vw |
| 5.94 | m–w | 2.96 | vw |
| 5.78 | m–w | 2.88 | vw |
| 5.50 | m–w | 2.75 | vw |
| 4.09 | vw | 2.74 | vw |
| 4.06 | vw | | |

EXAMPLE 5

Preparation of B-UTD-1

The borosilicate B-UTD-1 was prepared by combining 1.57 grams of a 20% Cp*$_2$CoOH aqueous solution with 6 mL of deionized water, 0.027 grams of NaOH and 0.025 grams of boric acid Then 0.405 grams of fumed silica were added to the mixture followed by stirring at room temperature for two hours. The gel having a molar ratio of SiO$_2$ : B$_2$O$_3$: Cp*$_2$CoOH: Na$_2$O: H$_2$O=1: 0.03: 0.13 : 0.05: 60 was transferred to a 23 mL Teflon-lined autoclave and heated under static conditions at 175° C. for 80 hours. The crystallization mixture was cooled to room temperature. The yellow crystals were isolated by suction filtration, washed with deionized water and dried at 90° C. for 15 hours. Elemental analysis indicated 35.7% Si, 0.25% B, 2.65% Co by weight.

TABLE 14

X-Ray Diffraction Pattern for B-UTD-1

| Interplanar d-spacing (Å) | Relative intensity | Interplanar d-spacing (Å) | Relative intensity |
|---|---|---|---|
| 14.66 | s | 3.66 | m |
| 11.72 | m | 3.61 | m |
| 8.07 | vw | 3.38 | w |
| 7.30 | m | 3.19 | w |
| 6.06 | vs | 3.12 | w–m |
| 5.87 | w | 3.08 | w |
| 4.95 | w | 3.00 | w–m |
| 4.88 | s | 2.79 | w |
| 4.54 | s | 2.76 | w |
| 4.35 | w | 2.73 | vw |
| 4.18 | vs | 2.63 | vw |
| 4.02 | m | 2.50 | vw |
| 3.93 | w–m | 2.49 | vw |
| 3.82 | w | 2.44 | vw |

TABLE 15

X-Ray Diffraction Pattern B-UTD-1 as Calcinated at 500° C.

| Interplanar d-spacing (Å) | Relative intensity | Interplanar d-spacing (Å) | Relative intensity |
|---|---|---|---|
| 14.61 | vs | 3.84 | vw |
| 11.52 | m | 3.65 | w |
| 9.45 | vw | 3.55 | w |
| 6.07 | w | 3.41 | w |

TABLE 15-continued

X-Ray Diffraction Pattern B-UTD-1 as Calcinated at 500° C.

| Interplanar d-spacing (Å) | Relative intensity | Interplanar d-spacing (Å) | Relative intensity |
|---|---|---|---|
| 4.87 | w | 3.34 | vw |
| 4.47 | w | 3.15 | vw |
| 4.37 | vw | 3.06 | vw |
| 4.19 | m | 2.98 | vw |
| 4.03 | w | 2.76 | vw |
| 3.94 | vw | | |

EXAMPLE 6

Preparation of B-UTD-1

2.6 grams of an aqueous 20% Cp*$_2$CoOH solution were mixed with 0.037 grams of boric acid. 2.109 g of tetraethylorthosilicate (TEOS) were added to the mixture followed by stirring for 15 minutes at room temperature. The mixture was then gradually heated to 80° C. to remove ethanol. After 30 minutes of stirring the mixture become very viscous and transparent. 7 grams of deionized water were added dropwise with stirring using a Teflon rod. The mixture was then cooled to room temperature and stirred for additional three hours. The final gel had a molar ratio of SiO$_2$ : B$_2$O$_3$ : Cp*$_2$CoOH : H$_2$O=1: 0.03 : 0.15 : 50. The gel was then transferred to 23 mL Teflon-lined autoclave and heated under static conditions at 175° C. for 7 days. The mixture was then cooled to room temperature. The yellow solid B-UTD-1 was isolated by suction filtration, washed with deionized water and dried at 90° C. for 15 hours. Elemental analysis indicated 37.3% Si, 0.31% B, 2.9% Co by weight.

TABLE 16

X-Ray Diffraction Pattern B-UTD-1

| Interplanar d-spacing (Å) | Relative intensity | Interplanar d-spacing (Å) | Relative intensity |
|---|---|---|---|
| 14.63 | s | 3.66 | m |
| 11.72 | m | 3.60 | m |
| 8.07 | vw | 3.44 | vw |
| 7.30 | w–m | 3.38 | w |
| 6.04 | m–s | 3.19 | vw |
| 5.86 | w | 3.13 | w–m |
| 4.95 | w | 3.08 | w |
| 4.88 | m | 3.00 | w–m |
| 4.54 | m | 2.79 | w |
| 4.35 | w | 2.76 | w |
| 4.19 | vs | 2.73 | vw |
| 4.03 | m | 2.63 | vw |
| 3.94 | w–m | 2.48 | vw |
| 3.82 | w | 2.49 | vw |

TABLE 17

X-Ray Diffraction Pattern for B-UTD-1 Calcinated at 500° C.

| Interplanar d-spacing (Å) | Relative intensity | Interplanar d-spacing (Å) | Relative intensity |
|---|---|---|---|
| 14.62 | vs | 3.84 | vw |
| 11.52 | m | 3.65 | w |
| 9.44 | vw | 3.55 | w |
| 6.07 | w | 3.39 | w |
| 4.87 | w | 3.34 | vw |
| 4.47 | w | 3.15 | vw |
| 4.37 | vw | 3.06 | vw |
| 4.21 | m | 2.98 | vw |
| 4.04 | w | 2.76 | vw |
| 3.95 | vw | | |

EXAMPLE 7

Preparation of V-UTD-1 (A)

The vanadium silicate V-UTD-1 was prepared by combining 3.46 grams of an aqueous 19% Cp*$_2$CoOH solution with 2.81 grams of tetraethylorthosilicate (TEOS) at room temperature. The mixture was then gradually heated to 70° C. to remove ethanol. Once the mixture became homogeneous and transparent, 7 mL of deionized water were added to it dropwise with stirring. The transparent silicate gel was then cooled to 45° C. and stirred for one hour. 0.025 grams of vanadyl sulfate (VOSO$_4$~3H$_2$O) were dissolved in 2.35 mL of deionized water and the solution was added dropwise to the silicate gel at 45° C. After adding each drop, the gel become cloudy and within a few seconds, turned transparent again. The final vanadium silicate gel having a molar ratio of SiO$_2$ : VO$_2$ : Cp*$_2$CoOH : H$_2$O=1: 0.0086 : 0.14: 50 was aged for two hours and then transferred to a 23 mL Teflon-lined autoclave. The gel was heated under static conditions at 175° C. for 7 days. The crystallization mixture was cooled to room temperature and the yellow solid V-UTD-1 was isolated by suction filtration, washed with deionized water and dried at 90° C. for 15 hours. Elemental analysis indicated 37.3% Si, 0.2% V, 2.2% Co by weight.

TABLE 18

X-Ray Diffraction Pattern V-UTD-1

| Interplanar d-spacing (Å) | Relative intensity | Interplanar d-spacing (Å) | Relative intensity |
|---|---|---|---|
| 14.66 | vs | 3.67 | vs |
| 11.74 | s | 3.61 | m |
| 7.31 | m | 3.39 | w |
| 6.06 | vs | 3.20 | vw |
| 5.87 | w | 3.13 | w–m |
| 4.96 | m | 3.09 | w |
| 4.90 | vs | 3.01 | m |
| 4.56 | vs | 2.80 | w |
| 4.37 | w | 2.77 | w |
| 4.20 | s | 2.51 | vw |
| 4.04 | m | 2.45 | vw |
| 3.93 | w–m | 2.41 | vw |

TABLE 19

X-Ray Diffraction Pattern for V-UTD-1 Calcinated at 500° C.

| Interplanar d-spacing (Å) | Relative intensity | Interplanar d-spacing (Å) | Relative intensity |
|---|---|---|---|
| 14.63 | vs | 3.96 | vw |
| 11.52 | m | 3.84 | vw |
| 9.48 | vw | 3.66 | w |
| 6.09 | vw | 3.56 | w |
| 4.88 | w | 3.40 | vw |
| 4.48 | w | 3.16 | w |
| 4.38 | vw | 3.07 | vw |

TABLE 19-continued

X-Ray Diffraction Pattern for V-UTD-1 Calcinated at 500° C.

| Interplanar d-spacing (Å) | Relative intensity | Interplanar d-spacing (Å) | Relative intensity |
|---|---|---|---|
| 4.22 | w | 2.99 | vw |
| 4.05 | vw | 2.77 | vw |

Preparation of V-UTD-1 (B)

The silicate gel was prepared by combining 0.81 grams of fumed silica with 2.67 grams of an aqueous 25% $Cp*_2CoOH$ solution and NaOH solution (0.054 grams NaOH in 6 mL $H_2O$). 0.059 grams of $VOSO_4 \cdot 3H_2O$ were dissolved in 4 mL of deionized water and the solution was added to the silicate gel. After one hour stirring at room temperature, the gel having a molar ratio of $SiO_2 : VO_2 : Cp*_2CoOH : Na_2O: H_2O = 1: 0.02 : 0.14 : 0.05 : 50$ was then transferred to a 23 mL Teflon-lined autoclave and heated under static conditions at 175° C. for three days. The crystallization mixture was cooled to room temperature. The yellow solid V-UTD-1 was isolated by suction filtration, washed with deionized water and dried at 90° C. for 15 hours.

TABLE 20

X-Ray Diffraction Pattern for V-UTD-1

| Interplanar d-spacing (Å) | Relative intensity | Interplanar d-spacing (Å) | Relative intensity |
|---|---|---|---|
| 14.79 | vs | 3.67 | s |
| 11.81 | s | 3.62 | m |
| 8.05 | vw | 3.45 | vw |
| 7.34 | m | 3.39 | w |
| 6.07 | vs | 3.20 | vw |
| 5.89 | w | 3.13 | w–m |
| 4.98 | w | 3.08 | w |
| 4.90 | vs | 3.01 | w–m |
| 4.56 | vs | 2.80 | w |
| 4.37 | w | 2.77 | w |
| 4.19 | s | 2.74 | vw |
| 4.03 | m | 2.51 | vw |
| 3.93 | w–m | 2.49 | vw |
| 3.82 | vw | 2.45 | vw |
| 3.72 | vw | | |

TABLE 21

X-Ray Diffraction Pattern for V-UTD-1 Calcinated at 500° C.

| Interplanar d-spacing (Å) | Relative intensity | Interplanar d-spacing (Å) | Relative intensity |
|---|---|---|---|
| 14.57 | vs | 3.95 | vw |
| 11.48 | m | 3.84 | vw |
| 9.45 | vw | 3.66 | w |
| 6.08 | w | 3.56 | w |
| 4.88 | w | 3.40 | vw |
| 4.47 | w | 3.16 | w |
| 4.38 | vw | 3.05 | vw |
| 4.20 | w | 2.98 | vw |
| 4.05 | vw | 2.77 | vw |

EXAMPLE 8

The oxidation of cyclohexane was carried out as a batch reaction in sealed glass vials (15 mL) under a nitrogen atmosphere. The vial was charged with 0.10 grams of Ti-UTD-1 catalyst, 5.28 mmol of cyclohexane substrate and 45 mmol of 90% t-BOOH. The mixture was heated with stirring at 60° C. and sampled by syringe through a rubber septum. Products were analyzed by gas chromatography. After 6 days there was 84% conversion of the cyclohexane with 12% selectivity for adipic acid.

All of the compositions and methods disclosed and claimed herein can be made and executed without undue experimentation in light of the present disclosure. While the compositions and methods of this invention have been described in terms of preferred embodiments, it will be apparent to those of skill in the art that variations may be applied to the compositions, methods and in the steps or in the sequence of steps of the methods described herein without departing from the concept, spirit and scope of the invention. More specifically, it will be apparent that certain agents which are chemically related may be substituted for the agents described herein while the same or similar results would be achieved. All such similar substitutes and modifications apparent to those skilled in the art are deemed to be within the spirit, scope and concept of the invention as defined by the appended claims.

REFERENCES

The following literature citations as well as those cited above are incorporated in pertinent part by reference herein for the reasons cited in the above text.

K. J. Balkus, Jr., and A. G. Gabrielov, J. Porous Mater., 1 (1995) 199.

K. J. Balkus, Jr., A. G. Gabrielov and S. Shepelev, Micropor. Mater., 3 (1995A) 665.

K. J. Balkus, Jr., A. G. Gabrielov, and N. Sandler, Mater. Res. Soc. Symp. Proc., 368 (1995B) 369.

K. J. Balkus, Jr., A. G. Gabrielov and S. I. Zones, Petrol. Preprints, 40 (1995C) 296.

K. J. Balkus, Jr., A. G. Gabrielov and S. I. Zones, Stud. Surf. Sci. Catal., 97 (1995D) 519.

K. J. Balkus, Jr. and S. Shepelev, Micropor. Mater., 1 (1993) 383.

A. Corma, M. T. Navarro and J. Peres-Pariente, J. Chem. Soc., Chem. Comm., (1994) 147.

J. Haggin, C&EN, November 13, 1995, 6.

J. Klaas, K. Kulawik, G. Schultz-Ekloff and N. I. Jaeger, Stud. Surf. Sci. Catal., 84 (1994) 2261.

R. Kumar, A. Raj, S. Baran Kumar and P. Ratnasamy, Stud. Surf. Sci. Catal., 84 (1994) 109.

T. Maschemeyer, F. Rey, G. Sankar and J. M. Thomas, Nature, 378 p. 159–162 (1995).

U. Schuchardt, H. O. Pastore and E. V. Spinace, Stud. Surf. Sci. Catal., 84 (1994) 1877.

T. Tatsumi, K. Asano and K. Yanagisawa, Stud. Surf. Sci. Catal., 84 (1994) 1861.

E. W. Valyocsik, U.S. Pat. No. 4,556,549 (1985).

E. W. Valyocsik, U.S. Pat. No. 4,568,654 (1986).

G. van de Goor, C. C. Freyhardt and P. Behrens, Z. Anorg. Allg. Chem., 621 (1995) 311.

L. T. Yuen, S. I. Zones, T. V. Harris, E. J. Gallegos and A. Auroux, Micropor. Mater., 2 (1994) 105.

What is claimed is:

1. A metal microcrystalline silica molecular sieve composition comprising a high silica zeolite UTD-1 molecular sieve having parallel channels with a nominal pore diameter greater than about 7.2 A and which incorporates a metal into the zeolite framework wherein said composition functions as a catalyst.

2. The composition of claim 1 which is prepared from a bis(pentamethylcyclopentadienyl)cobalt (III) ion template in the presence of a redox active metal.

3. The composition of claim 1 wherein the metal is identified as an oxidizable metal with incomplete d- or f-shell electrons.

4. The composition of claim 1 wherein the metal is selected from the group consisting of titanium, boron, vanadium, copper, cobalt, iron, chromium, manganese, zinc, aluminum and gallium.

5. The composition of claim 1 that as synthesized exhibits an x-ray powder diffraction patter as set forth in Table 5.

6. The composition of claim 5 calcined at about 500° C. which exhibits an x-ray powder diffraction pattern that includes the lines as set forth in Table 6.

7. The composition of claim 6 that includes about 3.5% titanium.

8. The composition of claim 5 further comprising $TiO_2$ and $Cp*_2CoOH$ of the formula $SiO_2:TiO_2:CP*_2CoOH:Na_2O:H_2O$ in a ratio of 1:0.033:0.014:0.05:40.

9. The composition of claim 6 that includes up to about 5% titanium.

10. The composition of claim 1 that as synthesized exhibits an x-ray powder diffraction pattern as set forth in Table 14.

11. The composition of claim 10 calcined at about 500° C. which exhibits an x-ray powder diffraction pattern that includes the lines as set forth in Table 15.

12. The composition of claim 11 that includes about 1.0% boron by weight.

13. The composition of claim 10 further comprising $B_2O_3$ and $Cp*_2CoOH$ in the formula $SiO_2:B_2O_3:Cp*_2CoOH:Na_2O:H_2O$ in a ratio of 1:0.03:0.13:0.05:60.

14. The composition of claim 1 that as synthesized exhibits an x-ray powder diffraction pattern as set forth in Table 18.

15. The composition of claim 14 calcined at about 500° C. which exhibits an x-ray powder diffraction pattern that includes the lines as set forth in Table 19.

16. The composition of claim 14 further comprising $VO_2$ and $Cp_2*CoOH_2$ in the formula $SiO_2:VO_2:Cp*_2CoOH:H_2O$ in a ratio of 1:0.0086:0.14:50.

17. A metal microcrystalline silica molecular sieve having a nominal pore diameter greater than about 7.2 A that incorporates a bis(pentamethylcyclopentadienyl)cobalt (III) ion as a guest molecule and that as synthesized exhibits an x-ray powder diffraction pattern as set forth in Table 13.

18. The silica molecular sieve of claim 17 further comprising $TiO_2$ and $Cp*_2CoOH$ in the formula $SiO_2:TiO_2:CP*_2CoOH:H_2O$ in a ratio of 1:0.062:0.14:50.

19. A method of oxidizing a substrate, comprising:
   a) Combining an oxidizable substrate, an oxidant and the molecular sieve of claim 1;
   b) Allowing oxidation to proceed for a time and at a temperature sufficient to allow oxidation to occur; and,
   c) Obtaining from the substrate at least one oxidized product.

20. The method of claim 19 wherein the oxidant is a peroxide.

21. The method of claim 20 wherein the oxidant is identified as tert-butyl hydroperoxide.

22. The method of claim 19 where the oxidant is dioxygen.

23. The method of claim 19 where the oxidant is hydrogen peroxide.

24. The method of claim 19 wherein the oxidizable substrate is identified as a hydrocarbon.

25. The method of claim 19 wherein the oxidizable substrate is cyclohexane.

26. The method of claim 19 wherein the molecular sieve composition is identified as the catalyst of claim 6 or claim 11 or claim 15.

27. The method of claim 19 wherein the molecular sieve composition includes cobalt incorporated into the zeolite framework.

28. The method of claim 19 wherein the molecular sieve composition includes titanium incorporated into the zeolite framework.

* * * * *

UNITED STATES PATENT AND TRADEMARK OFFICE
CERTIFICATE OF CORRECTION

PATENT NO. : 5,830,429
DATED : November 3, 1998
INVENTOR(S) : KENNETH J. BALKUS, JR. and ALEXEI G. GABRIELOV It is certified that error appears in the above-identified patent and that said Letters Patent is hereby corrected as shown below:

Col. 19, line 6, please delete "patter" and insert --pattern--.

Col. 19, line 14, please delete "$CP^*_2$" and insert --$Cp^*_2$--.

Col. 20, line 8, please delete "$CP^*_2$" and insert --$Cp^*_2$--.

Col. 20, line 19, please delete "tert-butyl" and insert --*tert*-butyl--.

Signed and Sealed this

Twenty-third Day of February, 1999

Attest:

Q. TODD DICKINSON

*Attesting Officer*  Acting Commissioner of Patents and Trademarks